(12) United States Patent
Canty et al.

(10) Patent No.: US 7,009,703 B2
(45) Date of Patent: Mar. 7, 2006

(54) GRANULAR PRODUCT INSPECTION DEVICE

(75) Inventors: Thomas M. Canty, Williamsville, NY (US); Paul J. O'Brien, East Aurora, NY (US); Christian P. Marks, Cheektowaga, NY (US); Richard E. Owen, Youngstown, NY (US)

(73) Assignee: J.M.Canty Inc., Buffalo, NY (US)

( * ) Notice: Subject to any disclaimer, the term of this patent is extended or adjusted under 35 U.S.C. 154(b) by 114 days.

(21) Appl. No.: 10/400,723

(22) Filed: Mar. 27, 2003

(65) Prior Publication Data

US 2004/0189991 A1 Sep. 30, 2004

(51) Int. Cl.
*G01N 15/02* (2006.01)

(52) U.S. Cl. .................................. 356/335; 356/237.1

(58) Field of Classification Search ........ 356/335–343, 356/600–622, 356, 237.1; 382/110, 141; 250/573, 574
See application file for complete search history.

(56) References Cited

U.S. PATENT DOCUMENTS

| | | | | |
|---|---|---|---|---|
| 4,121,294 A | | 10/1978 | Galanis et al. ............... | 364/571 |
| 4,288,162 A | * | 9/1981 | Sakamoto et al. ........... | 356/335 |
| 4,377,340 A | | 3/1983 | Green et al. ................. | 356/237 |
| 4,514,758 A | | 4/1985 | Berthel et al. ................ | 358/93 |
| 5,011,285 A | * | 4/1991 | Jorgensen et al. ........... | 356/335 |
| 5,023,714 A | | 6/1991 | Lemelson .................... | 358/107 |
| 5,519,793 A | * | 5/1996 | Grannes ...................... | 382/266 |
| 5,721,433 A | * | 2/1998 | Kosaka ........................ | 250/573 |
| 5,936,725 A | * | 8/1999 | Pike et al. ................ | 356/237.1 |
| 6,049,381 A | * | 4/2000 | Reintjes et al. ............. | 356/335 |
| 6,061,130 A | * | 5/2000 | Plate et al. .................. | 356/335 |
| 6,629,010 B1 | * | 9/2003 | Lieber et al. ............... | 700/109 |
| 2004/0151360 A1 | * | 8/2004 | Pirard et al. ................. | 382/141 |

FOREIGN PATENT DOCUMENTS

| | | |
|---|---|---|
| DE | 19832856 | 1/2000 |
| JP | 405045274 A * | 2/1993 |
| WO | WO 97/14950 | 4/1997 |
| WO | WO 02/44692 | 6/2002 |

OTHER PUBLICATIONS

"Particle Sizing Software", Canty Process Technology; Reference Data Sheet 99A8035 A8356, www.jmcanty.com/overview/V.Vector/a8356.pdf, J.M. Canty Inc.

"WipFrag System II—Online fragmentation analysis", Maerz, N. H., and Palangio, T. C., FRAGBLAST 6, Sixth International Symposium For Rock Fragmentation By Blasting, Johannesburg, South Africa, Aug. 8-12, 1999, pp. 111-115.

"Case studies using the WipFrag Image analysis system", Palangio, T. C. and Maerz, N. H., 1999, FRAGBLAST 6, Sixth International Symposium For Rock Fragmentation By Blasting, Johannnesburg, South Africa, Aug. 8-12, 1999, pp. 117-120.

(Continued)

*Primary Examiner*—Hoa Q. Pham
(74) *Attorney, Agent, or Firm*—Davidson, Davidson & Kappel, LLC

(57) ABSTRACT

A particle inspection device includes a feeder configured to drop a particle through an image area, a reflector configured to provide a reflected view of the particle in the image area, and an image capturing device configured to capture an image of the particle in the image area such that the image includes at least a direct view of the particle and the reflected view of the particle. In addition, a method for inspecting a particle includes dropping the particle through an image area, providing a reflected view of the particle in the image area using a reflector, and capturing an image of the particle in the image area using an image capturing device so that the image includes a direct view of the particle and the reflected view of the particle.

30 Claims, 4 Drawing Sheets

OTHER PUBLICATIONS

"Reconstructing 3-D block size distributions from 2-D measurements on sections", Maerz, N. H., 1996, Proceedings of the FRAGBLAST 5 Workshop on Measurement of Blast Fragmentation, Montreal, Quebec, Canada, Aug., 23-24, 1996, pp. 39-43.

"Image sampling techniques and requirements for automated image analysis of rock fragmentation", Maerz, N. H., 1996, Proceedings of the FRAGBLAST 5 Workshop on Measurement of Blast Fragmentation, Montreal, Quebec, Canada, Aug., 23-24, 1996, pp. 115-120.

"WipFrag Image based granulometry system", Maerz, N. H., Palanglo, T. C., and Franklin, J. A., 1996, Proceedings of the FRAGBLAST 5 Workshop on Measurement of Blast Fragmentation, Montreal, Quebec, Canada Aug., 23-24, 1996, pp. 91-99.

"Rocksizer Lab Test Report", Apr. 2001, J.M. Canty Inc., www.jmcanty.com/ApplicationInfor/reports/Rocksizer%20Lab%20Test%20Report.pdf.

"Dynamic Image Analysis: Improving Size Measurement of Nonspherical Particles", Ren Xu and Joe Santana, Beckman Coulter, Powder and Bulk Engineering, www.powderbulk.com/main/archive/02_february_02/beckman.html.

"Size and Shope Measurement" PartAn—Video Image Analysis, www.sci-tec-inc.com/image.html.

"Automated Imaging Technology for Particle Shape Analysis", David Higgs, Malvern Instruments Ltd., UK, Apr. 2002, www.currentdrugdiscovery.com.

"Camsizer Digital Image Processing Particle Size Analyzer", Horiba Instruments Inc., www.horibalab.com/Products/camsizer.html.

"Automatic Image Analysis", Working Group Mechanic of Bulk Material, www.mvt.-iw.uni-halle.de/forschung/labor/bild_e.html.

"Testing Road Aggregate Shape Using Digital Imaging", Canada's "Rock to Road" Magazine, www.rockroad.com/testing.html.

"Optical digital fragmentation measuring systems—inherent sources of error", Maerz, N. H., and Zhou, W., 1998, FRAGBLAST, The International Joun Fragmentation, vol. 2, No. 4, pp. 415-431.

* cited by examiner

GRANULAR PRODUCT INSPECTION DEVICE

BACKGROUND OF THE INVENTION

The present invention relates generally to inspection systems and particularly to a method and device for three-dimensional inspecting of particles.

It is often desirable to inspect particles that are produced or created during various industrial processes. Inspection may be useful for determining properties of the particles, including, for example, size, shape, purity, surface roughness, color, and uniformity. The particles may be inspected for a variety of reasons, for example, as part of a quality control process, for sorting, or for identifying particular qualities of the particles including defects.

Several devices and methods are known for inspecting and analyzing particles. For example, many such methods and devices employ laser diffraction, spectroscopy, and various forms of visual image analysis.

One known image analysis technique of particle inspection captures a two-dimensional image of particles being inspected as they fall from a feeder through an image area. The captured image is analyzed using software running on a microprocessor to determine certain properties of the particles, such as size and shape. For non-spherical particles, for example, rock fragments and particles produced in mining and aggregate industries, analysis of a two-dimensional image can lead to an incorrect determination of the true size or shape of the particle.

One known inspection system uses three-dimensional image analysis to inspect the shape of coarse aggregates. That known system relies on the analysis of two separate images taken at right angles from two separate cameras of aggregate particles moving on a conveyor belt. The use of separate cameras and separate images has several disadvantages including additional cost of the inspection device as well problems in calibrating the two separate images. In addition, obtaining high image quality of particles as they are being transported on a conveyor belt can be problematic and can diminish the accuracy and precision of the particle observations and/or measurements.

SUMMARY OF THE INVENTION

An object of the present invention is to provide a method and device for three-dimensional inspection of particles in an efficient and cost effective manner. A further object of the present invention is to provide a method and device that presents particles for inspection in an advantageous way for capturing high quality images of the particles.

The present invention provides a particle inspection device that includes a feeder configured to drop a particle through an image area, a reflector configured to provide a reflected view of the particle in the image area, and an image capturing device configured to capture an image of the particle in the image area such that the image includes at least a direct view of the particle and the reflected view of the particle. In this manner, the present invention provides a device in which a single image capturing device can obtain an image of the particle in free-fall that includes three-dimensional information about the particle being inspected. Particularly when non-spherical particles are being inspected, information about a third dimension of a particle may be especially advantageous to the particle inspection.

The reflector may be advantageously disposed in a field of view of the image capturing device such that a vertical axis of the reflector is perpendicular to a sighting axis of the image capturing device. When the reflector is disposed vertically with respect to the sighting axis of the image capturing device and in the field of view, the vertical position of the particle in the image will be the same in both the direct and reflected views. Thus the direct and reflected views of the particle are easily correlated with one another. If the angle of the vertical axis is not perfectly perpendicular to the sighting axis of the image capturing device, the analysis software may include a calibrating routine in order to correlate the direct and reflected views to the particle. Preferably, the reflector is also disposed so that the reflected view is a reflected side view of the particle. Though a reflected view of the particle from nearly any angle will provide additional information about the particle, a side view provides a full view of the dimension perpendicular to the front face of the particle.

The device preferably also includes a first light source disposed opposite the image capturing device that is configured to provide a backlighting for the direct view, and may further include a second light source disposed opposite the reflector and configured to provide a further backlighting for the reflected view. The first and second light sources may include illuminated panels, which may be LED panels. The backlighting provides an improved image of the profile of the direct and/or reflected views of the particle, which is advantageous, for example when inspecting for particle size and/or shape. If surface characteristics are desired to be inspected, front lighting may be provided in place of and/or in addition to the backlighting of the direct and reflected views.

The feeder preferably includes a tray surface angled downward toward a first end of the feeder disposed above the image area and the particle inspection device preferably also includes a vibration device configured to jog the particle toward the first end of the feeder. The first end of the feeder may advantageously include a downwardly curved edge portion. A first section of the curved edge portion is preferably tangential to the tray surface, and a second section of the curved edge portion is preferably tangential to a drop angle of the particle. The curved portion of the end of the feeder is preferably shaped so as to encourage a translation of the particle and to discourage a rotation of the particle, so that the particle slides off the end of the tray with minimal rotational movement as it falls. If the end of the tray ends abruptly, with no curved transition surface, the particles, particularly oblong-shaped particles, will tend to tumble as they fall through the image area. If the particle is tumbling during its free-fall through the image area, the orientation of the particle with respect to the image capturing device is not well-controlled, and is unlikely to include a principal face of the particle. Particularly when inspecting particles having elongated shapes, it is desirable to have at least one view that shows a principle face of the particle. As the particle vibrates along the tray surface, it will tend to settle in a position such that its principal face is facing downwards against the tray surface. When the particle reaches the curved edge portion, it will tend to slide along the curved edge portion with the principal face facing the surface of the curved edge portion. Thus, as the particle slides down the curved edge surface, the principle face is slowly being rotated so as to be facing the image capturing device as it falls from the end of the curved edge portion and through the image area.

The particle inspection device preferably also includes an image processing device in operative connection with the image capturing device, wherein the image processing device is configured to determine a property of the particle.

The property may includes a size property, a shape property, a color property, and a surface roughness property, or any combination of these. The image processing device is preferably configured to make calculations to derive further properties of the device, including, for example, volume and weight of the particle and statistical analyses based on the distribution of properties among large number of inspected particles.

The particle inspection device is preferably configured to inspect many particles, and the feeder is preferably configured to drop a second plurality of particles through the image area. The image capturing device is preferably configured to provide an image that includes a direct view of the particle and of the second plurality of particles and a reflected view of the particle and of the second plurality of particles. The flow rate of the particle being jogged through the feeder may be adjusted (for example by adjusting the vibrations of the vibration device and/or the angle of the feeder), so that more or less particles are captured in the image area by the image capturing device.

The device may also include a second image capturing device configured to capture a second image of a second particle in a second image area and wherein the second image includes a direct view of the second particle and a reflected view of the second particle. The use of more than one image capturing device may provide calibration advantages and may increase the rate at which images can be captured and processed and therefore the rate at which a large number particles can be inspected.

The image capturing device is preferably disposed such that a sighting axis of the image capturing device is substantially perpendicular to a drop angle of the particle. In most cases, the motion of the particle as it falls from the end of the tray surface will include a horizontal component and therefore the drop angle will not be vertical, at least not at the upper part of its free fall. Therefore, the image capturing device is preferably disposed so that the sighting axis is at an angle from horizontal.

The present invention also provides a method for inspecting a particle. The method includes the steps of dropping the particle through an image area, providing a reflected view of the particle in the image area using a reflector, and capturing an image of the particle in the image area using an image capturing device such that the image includes a direct view of the particle and the reflected view of the particle.

The dropping is preferably performed using a feeder having a downwardly curved edge portion. Also, the dropping is preferably performed so that a principle face of the particle is oriented so as to be facing the image capturing device. Backlighting is also preferably provided to the direct and/or reflected views, when size and shape characteristics of the particle are desired. The backlighting is preferably provided using one or more panels, such as LED panels. The method may further include analyzing the direct view and the reflected view of the image so as to determine a property of the particle, the analyzing preferably being performed using a microprocessor. The method preferably also includes dropping a second plurality of particles through the image area so that the image includes a direct view of the particle and the second plurality of particles and a reflected view of the particle and the second plurality of particles.

The method may be performed on a particle having a major diameter between 50 microns and 6000 microns, and/or on a particle has a major diameter between 0.1 inches and 3.0 inches, and/or on a particle having a major diameter greater than 1 inch.

BRIEF DESCRIPTION OF THE DRAWINGS

The present invention will be discussed in the following with reference to the drawings, in which.

DETAILED DESCRIPTION

Figure 1:
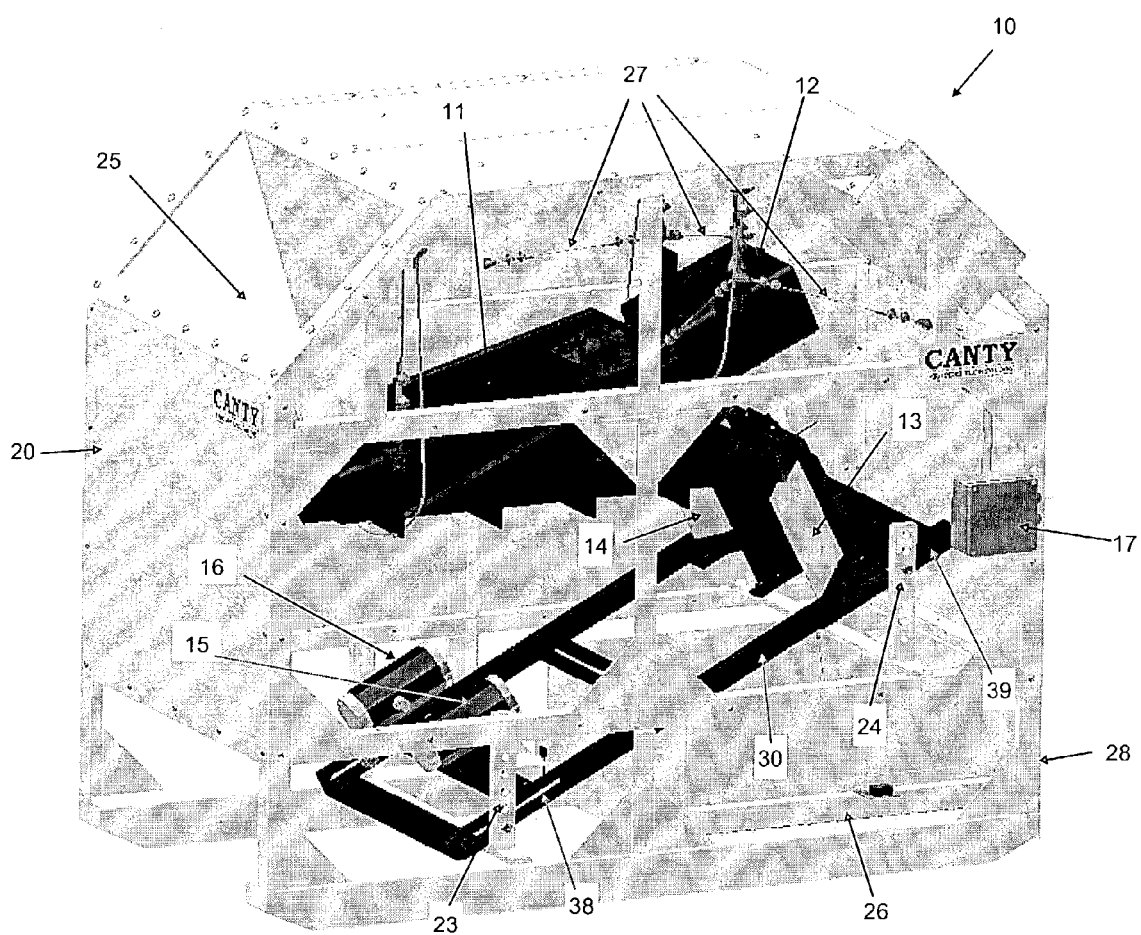
FIG. 1 shows a perspective view of a particle inspection device according to the present invention.

FIG. 1 shows a perspective view of one embodiment of a particle inspection device 10, which includes housing 20. Inside the housing, a feeder 11 is suspended from the housing using mounting cables 27. A vibration device 12 is rigidly connected to the feeder 11 and also suspended from the housing 10 using mounting cables 27. A particle inlet opening 25 enables particles to be placed into the feeder 11. In a laboratory setting, a user of the device may place a sample of particles to be inspected through the particle inlet opening 25. Alternatively, the device could be used in-line so that the particles flow through the opening from a previous process operation.

The feeder includes a tray surface that is preferably slightly inclined downward from the end proximate the particle inlet opening 25. When particles are in the feeder 11 and the vibration device 12 is switched on, such as by switching on switch 17, the feeder is vibrated by vibration device 12, which jostles the particles so that they may migrate toward the downward end of the feeder 11, which is adjacent the vibration device 12 in FIG. 1. When the particles reach the downward end of the feeder, the particles fall into catch tray 26. The particles can be removed from the housing through opening 28 in the rear of the housing by the device user. Alternatively, if the inspection device were to be used in-line with a larger production or inspection process, the particles could fall into a chute or otherwise flow to a subsequent process operation. An imaging assembly 30 is mounted to supports 23 and 24, which each include a plurality of holes, using bolts passing through slots 38 and 39 respectively, of imaging assembly 30. In this way, the imaging assembly 30 is mounted in a manner such that its position and angle can be adjusted to provide optimal viewing and imaging conditions.

Figure 2:
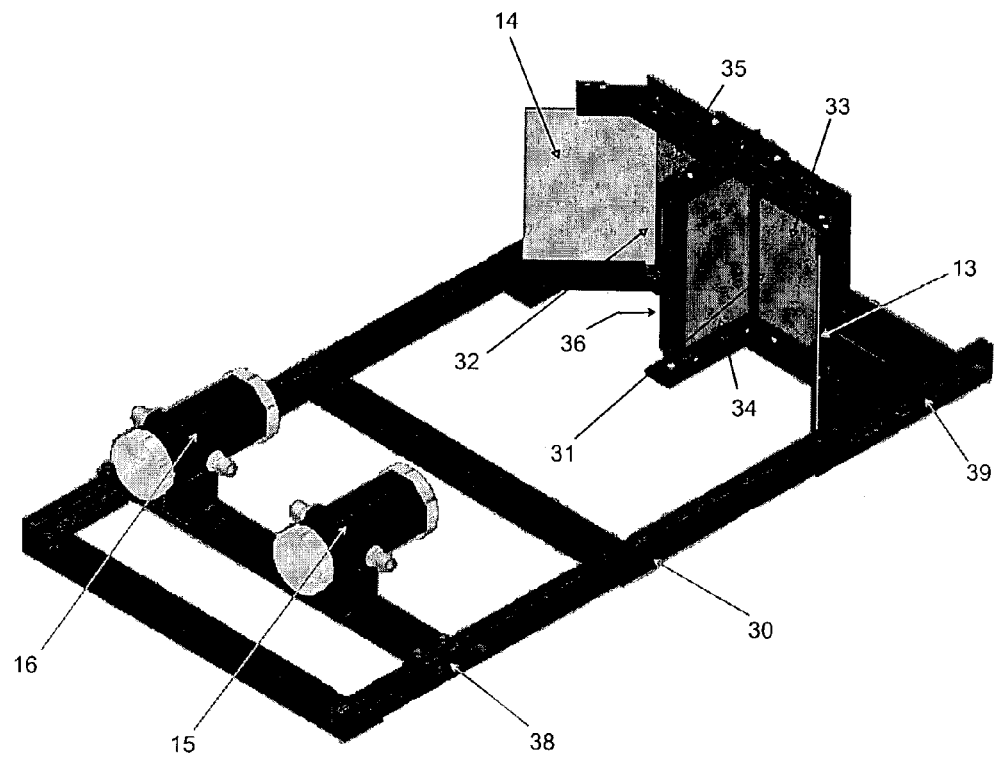
FIG. 2 shows a perspective view of the imaging assembly of the particle inspection device shown in FIG. 1.

Imaging assembly 30 is shown in more detail in FIG. 2. Two image capturing devices, for example CCD cameras 15 and 16, are mounted at one end of imaging assembly 30. At an opposite end, an illumination panel 33 is mounted opposite camera 15 and illumination panel 35 is mounted opposite camera 16. Image area 31 includes the area in front of illumination panel 33 through which particles fall from the feeder 11 to the catch tray 26. A second image area 32 includes the area in front of illumination panel 35 through which particles fall from the feeder 11 to the catch tray 26. Because the particles fall between a camera and illumination pair (15 and 33, or 16 and 35, respectively), the illumination panels 33 and 35, when illuminated, provide backlighting for a direct view of the particles from cameras 15 and 16, respectively. LED panels may be used as the illumination panels.

Although the embodiment shown includes a pair image capturing devices 15, 16 and a pair image areas 31, 32, this is not necessary for the functioning of the invention. An imaging assembly including a single image capturing device 15 and single image area 31 would work as well. The use of two cameras merely increases the rate at which particles can be inspected as two images can be captured of different particles and simultaneously processed.

In addition, imaging assembly 30 includes reflector 13, such as a mirror, which is positioned within a field of view of the first image capturing device 15 such that it provides a reflected side view of particles falling through the image area 31 to image capturing device 15. Illuminated panel 34, which is oriented 90 degrees with respect to illumination panel 33, provides backlighting to the reflected side view taken from camera 15. Similarly, reflector 14 is positioned within the field of view of second camera 16 such that it provides a reflected side view of particles falling through the second image area 32 to second camera 16. Illuminated panel 36, which is oriented 90 degrees with respect to illumination panel 35 (and back-to-back with respect to illumination panel 34) provides backlighting to the reflected side view taken from camera 16.

Figure 3:
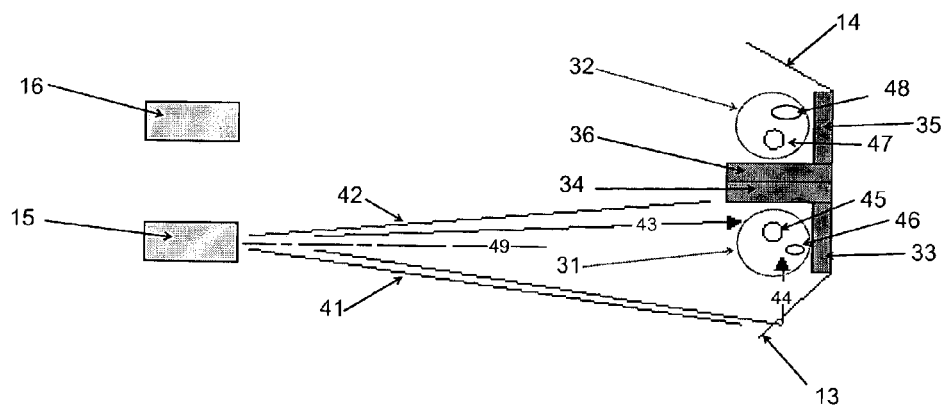
FIG. 3 shows a schematic view of a portion of the imaging assembly shown in FIG. 2.

FIG. 3 shows a schematic view of the components of the imaging assembly 30. Particles 45 and 46 are shown falling within first image area 31. Particles 47 and 48 are shown falling within second image area 32. First camera 15 defines sighting axis 49 and a field of view between boundary lines 41 and 42. The direct view 43 of the image area 31 taken from camera 15 is shown schematically by arrow 43 and the reflected side view taken from camera 15 is shown schematically by arrow 44.

Figure 4:
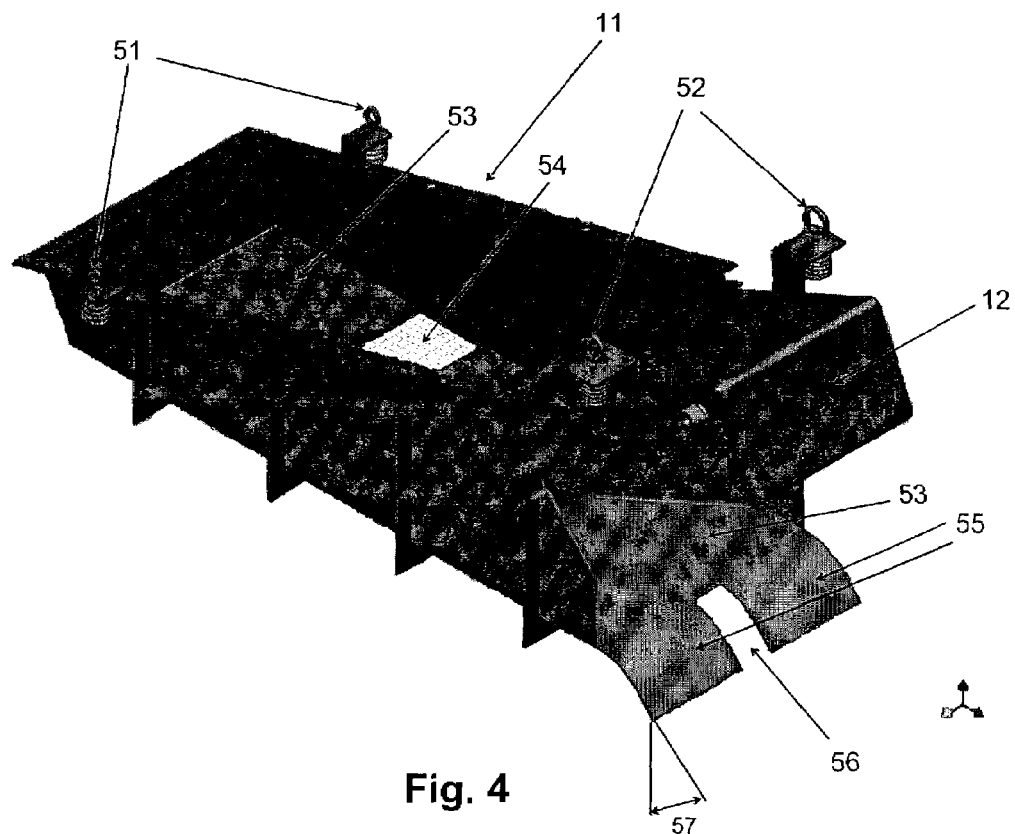
FIG. 4 shows a perspective view of the feeder and vibration device of the particle inspection device shown in FIG. 1.

The feeder 11 and vibration device 12 are shown in more detail in FIG. 4. Feeder 11 includes two mounting elements 51. Feeder 11 is rigidly attached to vibration device 12, which also includes two mounting elements 52. Mounting elements 51 and 52 each including a loop connected to a spring. Mounting cables 27 are connect to the loops of mounting elements 51 and 52 in order to suspend the feeder 11 and the vibration device 12 from the housing. The springs in mounting elements 51 and 52 provide damping action in order to smooth out the vibrations to feeder 11 and to allow a smoother migration of the particles from one end of the feeder to the other. Feeder 11 includes tray surface 53 at its bottom. Feeder is preferably disposed within housing 20 in such a manner that tray surface 53 slopes downward slightly toward the open end of the feed tray (disposed underneath vibration device 12 in FIG. 4). The slight downward slope coupled with the vibrations induces a migration of the particles from one end of the feeder to the other.

At its open end, tray surface 53 includes downwardly curved portion 55. Curved portion 55 provides a smooth transition to the particles as they fall off the edge of tray surface 53 and helps to orient the particles so that a principle surface of the particle is directed toward the camera during free-fall through the image area. Through the vibration of the feeder 1, the particles, which may include rock fragments or other particles having oblong shapes, will tend to settle into a position with their principle face (i.e. the face having the largest substantially flat surface area) downward. If the tray surface were to include an abrupt edge without a downwardly curved edge portion, the oblong-shaped particles would tend to tumble off the edge of the feeder and rotate end-over-end as they fell through the image area. In effect, the edge would act to flip the trailing edge upward as the leading edge of the particle began to fall. With the curved edge portion 55, the particles will tend to slide down the edge portion with their principle faces adjacent to the surface of the curved edge portion 55. Thus, as the particles slide down the curved edge portion, they become oriented such that their principal faces are facing toward image capturing device and in a direction perpendicular to the direction of movement of the particle as it begins to fall from the feeder. The end of the curvature of edge portion 55 is preferably tangential with the initial angle of fall 57 of the particle from feeder 11. In addition, imaging assembly 30 is preferably mounted within housing 20 so that the sighting axis of the camera is perpendicular to the direction of fall of the particles. In this way, the particles will tend to fall with only minimal rotational movement, if any. During the fall, the principal faces of the particles will be oriented substantially toward the camera. In this way, the direct view of the particle from the camera will show the principle face of the particle, which is useful, especially for size and shape determinations of oblong-shaped particles.

The direction of fall of the particle, will typically not be directly vertical, at least not during the upper portion of its fall. Rather, as it leaves the end of curved portion 55, the particle will be sliding along in the direction of the angle 57 of the curved portion. The direction of fall will become more vertical later in the fall as gravity accelerates the particle downward . Therefore, as shown in FIG. 1, in order to capture an image of the particles perpendicular to their direction of fall through the image area, the imaging assembly 30 is typically mounted in housing 20 at an angle from direct horizontal.

Tray surface 53 of feeder 11 also includes screened recess 54 at an intermediate portion between the two ends, which may be provided in order to remove particularly fine particles ("fines") from a particle sample being inspected. In some instances, the volume of fines that are mixed with the larger particles can create a "dirt curtain" through the image area, or otherwise interfere with optimal imaging of the larger particles. Depending on the type of particles being inspected, and the type of analysis being performed, the gage of the screened recess may be adjusted or a feeder without a screened recess may be used.

Figure 6:
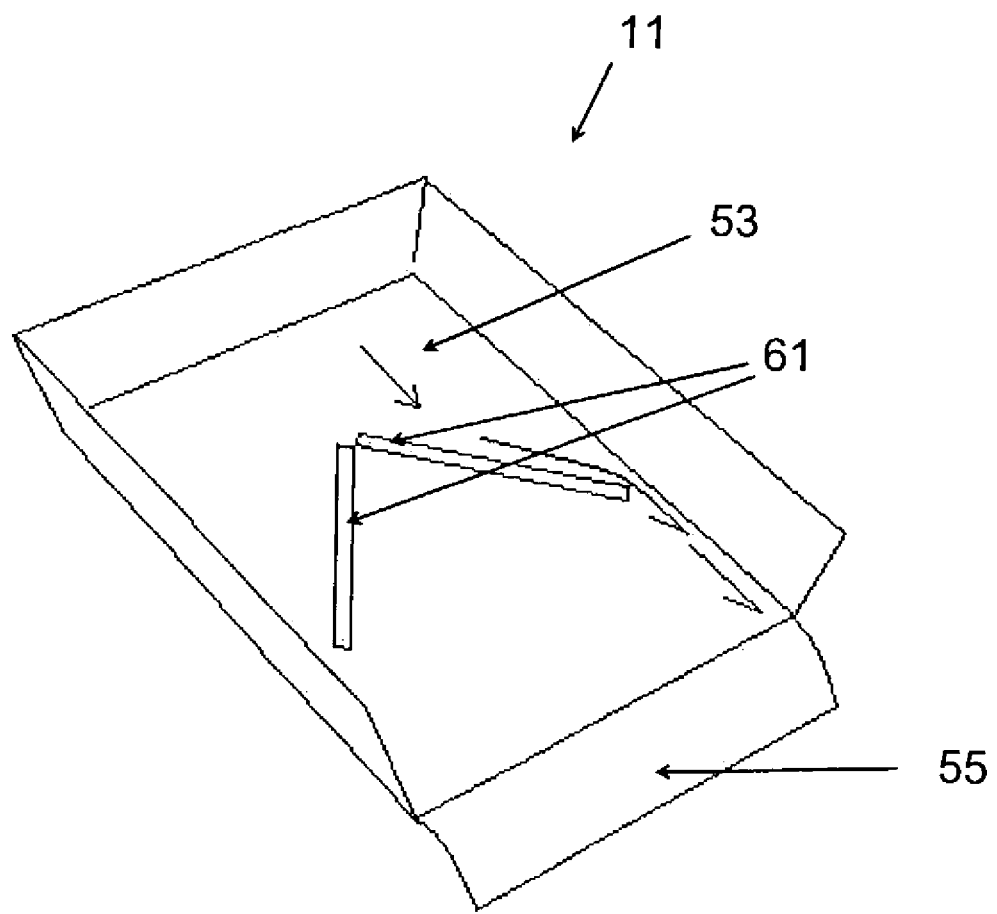
FIG. 6 show a perspective view of an exemplary embodiment of a gate mechanism.

A gating mechanism may be optionally used in the feeder with or without a screened recess to separate out particles according to size and/or to control the rate of migration of the particles through the feeder. One example of a gating mechanism, shown in FIG. 6, includes a low-profile raised portion 61 of tray surface 53 of the feeder. Raised portion 61 may be a strip of material connected, for example by welding, to tray surface 53. Raised portion 61 is sized so as to extend above the rest of surface 53 enough to divert fine particles toward the edges of tray surface 53 while enabling larger particles to vibrate over raised portion 61 without being significantly diverted. By diverting the fines to the edges of the tray surface 53, interference with the imaging of the larger particles is reduced or eliminated. The optimal height of raised portion 61 for diverting fine particles will depend on, among other factors, the size of particles being imaged and the size of fine particles to be diverted.

For applications in which the fines are an important component of the measurement, the fines can be extracted from the main flow, for example by using the screened recess 54, and sent down a chute so as to pass through a supplemental image area. A supplemental image capturing device may capture images of the fines and send them to the processor for inclusion in the total analysis of the sample.

Flow of fines through a supplemental image area may be viewed with backlighting and/or using a reflector as are the particles through the first and second image areas 31 and 32.

Figure 5:
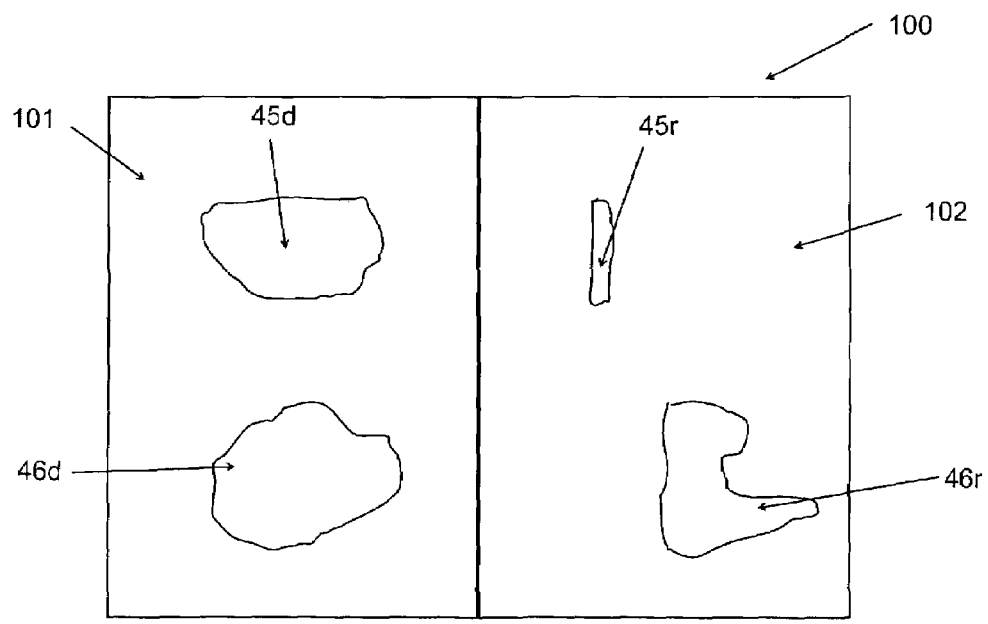
FIG. 5 shows a schematic view of an image captured from the particle inspection device shown in FIG. 1.

An example of an image 100 of particles 45 and 46 (as shown in FIG. 3) is shown in schematic form in FIG. 5. The left half of the image 100 shows a direct view 101 of image area 31 and the right half of the image shows a reflected view 102 of image area 31. 45d represents a direct view of particle 45 and 45r represents a reflected side view of particle 45. Likewise, 46d represents a direct view and 46r represents a reflected side view of particle 46. As can be seen from two views of the image, particle 45 has a rather flat shape with considerably less thickness than particle 46. The image 100, shows an example of the importance of the additional information shown in the reflected side view, especially in determining size or volume of the particles. For example, if only the direct view of the particles were available, the particle 46 may be judged to be only slightly larger than particle 45. When both views are available, it becomes clear that the volume of particle 46 is substantially greater than the volume of particle 45.

In the preceding specification, the invention has been described with reference to a specific exemplary embodiment thereof. It will, however, be evident that various modifications and changes may be made thereto without departing from the broader spirit and scope of the invention as set forth in the claims that follow. The specification and drawings are accordingly to be regarded in an illustrative rather than a restrictive sense.

What is claimed is:

1. A particle inspection device comprising:
   a feeder configured to drop a particle through an image area;
   a reflector configured to provide a reflected side view of the particle in the image area; and
   an image capturing device configured to capture an image of the particle in the image area, the image including at least a direct view of the particle and the reflected side view of the particle.

2. The particle inspection device as recited in claim 1 wherein the reflector is disposed in a field of view of the image capturing device such that a vertical axis of the reflector is perpendicular to a sighting axis of the image capturing device.

3. The particle inspection device as recited in claim 1 further comprising a first light source disposed opposite the image capturing device and configured to provide a backlighting for the direct view.

4. The particle inspection device as recited in claim 3 further comprising a second light source disposed opposite the reflector and configured to provide a further backlighting for the reflected view.

5. The particle inspection device as recited in claim 4 wherein the second light source includes a second illuminated panel.

6. The particle inspection device as recited in claim 5 wherein the first and second illuminated panels include LED panels.

7. The particle inspection device as recited in claim 3 wherein the first light source includes a first illuminated panel.

8. The particle inspection device as recited in claim 1 wherein the feeder includes a tray surface angled downward toward a first end of the tray surface disposed above the image area.

9. The particle inspection device as recited in claim 8 further comprising a vibration device configured to jog the particle toward the first end of the tray surface.

10. The particle inspection device as recited in claim 8 wherein the first end of the tray surface includes a downwardly curved edge portion.

11. The particle inspection device as recited in claim 10 wherein a first section of the curved edge portion is tangential to the other portion of the tray surface, and a second section of the curved edge portion is tangential to a drop angle of the particle.

12. The particle inspection device as recited in claim 11 wherein the curved edge portion is shaped so as to enable the particles to slide off the edge of the tray without inducing a rotational movement to the particles.

13. The particle inspection device as recited in claim 1 further comprising an image processing device in operative connection with the image capturing device, the image processing device configured to determine a property of the particle.

14. The particle inspection device as recited in claim 13 wherein the property includes at least one of a size property, a shape property, a color property, and a surface roughness property.

15. The particle inspection device as recited in claim 1 wherein the feeder is configured to drop a second plurality of particles through the image area and wherein the image includes a direct view of the particle and of the second plurality of particles and a reflected view of the particle and of the second plurality of particles.

16. The particle inspection device as recited in claim 1 further comprising a second image capturing device configured to capture a second image of a second particle in a second image area and wherein the second image includes a direct view of the second particle and a reflected view of the second particle.

17. The particle inspection device as recited in claim 1 wherein the image capturing device defines a sighting axis and is disposed such that the sighting axis is substantially perpendicular to a direction of fall of the particle.

18. The particle inspection device as recited in claim 17 wherein image capturing device is disposed so that the sighting axis is at an angle from horizontal.

19. A method for inspecting a particle comprising:
   dropping the particle through an image area using a feeder;
   providing a reflected side view of the particle in the image area using a reflector; and
   capturing an image of the particle in the image area using an image capturing device, wherein the image includes a direct view of the particle and the reflected side view of the particle.

20. The method as recited in claim 19 wherein the feeder has a downwardly curved edge portion.

21. The method as recited in claim 19 wherein the dropping of the particle includes dropping the particle such that a principle face of the particle is oriented so as to be facing the image capturing device.

22. The method as recited in claim 19 further comprising providing a first backlighting to the direct view and a second backlighting to the reflected view.

23. The method as recited in claim 22 wherein the providing of backlighting is performed using first and second illuminated panels.

24. The method as recited in claim 19 further comprising analyzing the direct view and the reflected view of the image so as to determine a property of the particle.

25. The method as recited in claim 24 wherein the analyzing is performed using a microprocessor.

26. The method as recited in claim 19 further comprising dropping a second plurality of particles through the image area and wherein the image includes a direct view of the particle and the second plurality of particles and a reflected view of the particle and the second plurality of particles.

27. The method as recited in claim 19 further comprising:
dropping a second particle through a second image area;
providing a reflected side view of the second particle in the second image area using a second reflector; and
capturing a second image of the second particle in the second image area using a second image capturing device, wherein the second image includes a direct view of the second particle and the reflected side view of the second particle.

28. The method as recited in claim 19 wherein the particle has a major diameter between 50 microns and 6000 microns.

29. The method as recited in claim 19 wherein the particle has a major diameter between 0.1 inches and 3.0 inches.

30. The method as recited in claim 19 wherein the particle has a major diameter greater than 1 inch.

* * * * *